(12) United States Patent
Konawa (10) Patent No.: US 11,020,291 B2
(45) Date of Patent: Jun. 1, 2021

(54) ABSORBENT ARTICLE

(71) Applicant: DAIO PAPER CORPORATION, Ehime (JP)

(72) Inventor: Satoko Konawa, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 600 days.

(21) Appl. No.: 15/557,500

(22) PCT Filed: Mar. 16, 2016

(86) PCT No.: PCT/JP2016/058326
§ 371 (c)(1),
(2) Date: Sep. 12, 2017

(87) PCT Pub. No.: WO2016/148194
PCT Pub. Date: Sep. 22, 2016

(65) Prior Publication Data
US 2018/0049929 A1    Feb. 22, 2018

(30) Foreign Application Priority Data

Mar. 16, 2015    (JP) .............................. JP2015-051894

(51) Int. Cl.
*A61F 13/534* (2006.01)
*A61F 13/535* (2006.01)
(Continued)

(52) U.S. Cl.
CPC ...... *A61F 13/534* (2013.01); *A61F 13/51104* (2013.01); *A61F 13/535* (2013.01); *A61F 2013/530481* (2013.01)

(58) Field of Classification Search
CPC ............................ A61F 13/534; A61F 13/535; A61F 13/51104; A61F 2013/530481;
(Continued)

(56) References Cited

U.S. PATENT DOCUMENTS

5,938,650 A * 8/1999 Baer .................... A61F 13/5323
604/368
9,044,359 B2 * 6/2015 Wciorka ............... A61F 13/495
(Continued)

*Primary Examiner* — Ariana Zimbouski
*Assistant Examiner* — Gabriella E Burnette
(74) *Attorney, Agent, or Firm* — Wenderoth, Lind & Ponack, L.L.P.

(57) ABSTRACT

An object of the invention is to improve the diffusibility of body fluid such that the body fluid can be quickly absorbed. The sanitary napkin 1 represented by FIG. 3 includes an absorbing body 4 with a highly water-absorbent polymer 12 interposed between an upper layer sheet 10 disposed on the skin side and a lower layer sheet 11 disposed on the non-skin side. The upper layer sheet 10 has a plurality of first protrusions 14 forming first space parts 13 that are to be filled with the highly water-absorbent polymer and that expand to the skin side, and a plurality of second protrusions 16 forming second space parts 15, each of which having a smaller volume than each of the first space part 13, that are to be filled with the highly water-absorbent polymer and that expand to the skin side. The weight per unit area of the highly water-absorbent polymer 12 filled into the second space parts 15 is made smaller than the weight per unit area of the highly water-absorbent polymer 12 filled into the first space parts 13.

5 Claims, 9 Drawing Sheets (51) Int. Cl.
*A61F 13/511* (2006.01)
*A61F 13/53* (2006.01)

(58) Field of Classification Search
CPC ...... A61F 13/5323; A61F 2013/530562; A61F 2013/53051; A61F 2013/530547
See application file for complete search history.

(56) References Cited

U.S. PATENT DOCUMENTS

| | | | |
|---|---|---|---|
| 9,566,198 B2* | 2/2017 | Wright | A61F 13/15658 |
| 2005/0003191 A1* | 1/2005 | Ehrnsperger | A61L 15/60 |
| | | | 428/403 |
| 2006/0240229 A1* | 10/2006 | Ehrnsperger | A61F 13/53 |
| | | | 428/195.1 |
| 2010/0004614 A1* | 1/2010 | Ashton | A61F 13/532 |
| | | | 604/367 |
| 2010/0209664 A1* | 8/2010 | Sato | B32B 3/266 |
| | | | 428/138 |
| 2010/0249740 A1* | 9/2010 | Miyamoto | A61F 13/51104 |
| | | | 604/384 |
| 2012/0316528 A1* | 12/2012 | Kreuzer | A61F 13/536 |
| | | | 604/366 |
| 2012/0323195 A1* | 12/2012 | Ehrnsperger | A61F 13/15203 |
| | | | 604/366 |
| 2013/0284362 A1* | 10/2013 | Tsujimoto | B23B 3/10 |
| | | | 156/276 |
| 2017/0239107 A1* | 8/2017 | Castrogiovanni | A61F 13/534 |

* cited by examiner

ABSORBENT ARTICLE

TECHNICAL FIELD

The present invention relates to an absorbent article such as a sanitary napkin, a panty liner and an incontinence pad. In more detail, the present invention relates to an absorbent article having an absorbing body with a highly water-absorbent polymer interposed between an upper layer sheet and a lower layer sheet.

BACKGROUND ART

Conventionally, as the absorbent article, an article with an absorbing body having functions of absorbing and retaining body fluid interposed between a liquid impermeable rear surface sheet such as a polyethylene sheet or a polyethylene sheet laminated nonwoven fabric and a liquid permeable front surface sheet such as a nonwoven fabric or a liquid permeable plastic sheet is known.

Numerous improvements have been made to this kind of the absorbent article, and as the absorbing body, an absorbing body having a structure where a highly water-absorbent polymer is disposed between two layers of sheets has been proposed. For example, in the following Patent Literature 1, an absorbent sheet material having a first sheet material and a second sheet material, wherein the cross-section of the first sheet material is a corrugated structure and the first sheet material is molded such that a plurality of corrugated groove structures are formed, a highly absorbent polymer is filled in the corrugated groove structures at 20 to 200 g/m², and the second sheet material is joined at the top of the respective corrugation of the corrugated groove structures of the first sheet material in which the highly absorbent polymer is filled, is disclosed.

In addition, in the following Patent Literature 2, an absorbent article having a top sheet, a back sheet and an absorbent laminate disposed between both sheets, wherein the absorbent laminate has an upper sheet-like absorbent layer, a fiber assembly layer and an lower sheet-like absorbent layer in this order from the top sheet side, wherein the fiber assembly layer includes pulp fiber, each of the upper sheet-like absorbent layer and the lower sheet-like absorbent layer includes water-absorbent resin between nonwoven fabric sheets but not pulp fiber, and each of the upper sheet-like absorbent layer and the lower sheet-like absorbent layer includes, between the nonwoven fabric sheets, a plurality of water-absorbent resin present regions where the absorbent resin is provided and a water-absorbent resin absent region adjacent to the water-absorbent resin present region, and the nonwoven fabrics are joined together at the water-absorbent resin absent region to form a sealing portion, is disclosed.

CITATION LIST

Patent Literature

Patent Literature 1: Japanese Patent Application Laid-Open Publication No. H08-299385
Patent Literature 2: Japanese Patent No. 5318747

SUMMARY OF INVENTION

Technical Problems

A characteristic of an absorbing body having a structure wherein a highly water-absorbent polymer is interposed between two layers of sheets is that the absorbing body can be made thinner in comparison to an absorbing body composed of an assembly of water-absorbing fiber such as pulp. However, the highly water-absorbent polymer is slower than pulp in the water absorption speed, and is also inferior in the diffusibility of body fluid. Accordingly, a problem has been pointed out that, when a large amount of body fluid is discharged at once, the body fluid cannot be quickly absorbed, and that the body fluid concentrates in a certain point, leading to the body fluid leaking in an overflowing manner.

With regards to this point, in the absorbent sheet material disclosed in the above-described Patent Literature 1, a highly water-absorbent polymer is filled in a plurality of corrugated groove structures, and therefore, an almost uniform amount of the highly water-absorbent polymer is disposed over almost the entire surface of the sheet. Accordingly, when a large amount of body fluid is discharged, there has been a high possibility that the body fluid cannot be quickly absorbed by the highly water-absorbent polymer and thus leading to leakage of the body fluid.

On the other hand, in the absorbent article disclosed in the above-described Patent Literature 2, by providing a water-absorbent resin absent region, the body fluid permeates the water-absorbent resin absent region such that the body fluid is absorbed by a fiber assembly layer which is the lower layer. However, the absorbent article does not have a structure where the body fluid can be absorbed efficiently only by a single sheet-shaped absorbent layer.

Therefore, a main object of the present invention is to provide an absorbent article having an absorbing body with a highly water-absorbent polymer interposed between an upper layer sheet and a lower layer sheet which makes it possible to improve the diffusibility of body fluids and to enable the body fluids to be quickly absorbed.

Solutions to Problems

In order to achieve the above-described object, as the present invention according to claim 1, an absorbent article including an absorbing body with a highly water-absorbent polymer interposed between an upper layer sheet disposed on the skin side and a lower layer sheet disposed on the non-skin side, wherein the upper layer sheet has a plurality of first protrusions forming first space parts that are to be filled with the highly water-absorbent polymer and that expand to the skin side, and a plurality of second protrusions forming second space parts, each of which having a smaller volume than each of the first space parts, that are to be filled with the highly water-absorbent polymer and that expand to the skin side, and the weight per unit area of the highly water-absorbent polymer filled into the second space parts is smaller than the weight per unit area of the highly water-absorbent polymer filled into the first space parts, is provided.

The invention according to the above-described claim 1 is an absorbent article including an absorbing body with a highly water-absorbent polymer interposed between an upper layer sheet disposed on the skin side and a lower layer sheet disposed on the non-skin side. The upper layer sheet has a plurality of first protrusions forming first space parts that are to be filled with the highly water-absorbent polymer and that expand to the skin side, and a plurality of second protrusions forming second space parts, each of which having a smaller volume than each of the first space parts, that are to be filled with the highly water-absorbent polymer and that expand to the skin side. Accordingly, it becomes easier for the body fluid to diffuse along the boundary portions between the first protrusions and the second protrusions, and it enables the body fluid to be quickly absorbed by the highly water-absorbent polymer having a large area.

Further, each of second space parts within the second protrusions has a smaller volume than each of first space parts within the first protrusions. Accordingly, when the planar shape of the first protrusions and that of the second protrusions are the same, the expansion height of the second protrusions towards the skin side is lower than that of the first protrusions, and therefore, it becomes easier for the body fluid to diffuse along the second protrusions which have lower heights. In addition, when the planar shape of the respective second protrusions is smaller than that of the first protrusions, it becomes easier for the body fluid to diffuse along the second protrusions which have smaller planar shapes. As such, it becomes easier for the body fluid to diffuse along the second protrusions, each of which having a relatively smaller volume than each of the first protrusions, and therefore, the body fluid can be quickly absorbed by the highly water-absorbent polymer having a large area.

Furthermore, in order not to hinder the diffusion of the body fluid along the second protrusions, the weight per unit area of the highly water-absorbent polymer filled into second space parts is made smaller than the weight per unit area of the highly water-absorbent polymer filled into first space parts. Accordingly, the diffusion of the body fluid along the second protrusions is improved, and the problem that the body fluid concentrates in a certain part such that the body fluid leaks in an overflowing manner can be solved.

As the present invention according to claim 2, the absorbent article according to claim 1, wherein the first protrusions are arranged around the second protrusions and parts in which the first protrusions do not intervene is provided between the adjacent second protrusions, is provided.

In the invention according to the above-described claim 2, the first protrusions are arranged around the second protrusions, and a part where the first protrusions do not intervene is provided between the adjacent second protrusions. Accordingly, it becomes easier for the body fluid to diffuse along the adjacent second protrusions through the part in which the first protrusions do not intervene, and the body fluid can be quickly absorbed by the highly water-absorbent polymer filled in the second protrusions.

As the present invention according to claim 3, the absorbent article according to claim 1, wherein the volume of the second space part is made smaller than the volume of the first space part by making the expansion height of the second protrusion towards the skin side lower than the expansion height of the first protrusion towards the skin side, by making the area of the planar shape of the second protrusion smaller than the area of the planar shape of the first protrusion, or by both of the above, is provided.

In the invention of the above-described claim 3, a means for making the volume of the second space part smaller than the volume of the first space part is defined. Specifically, the volume of the space part is made relatively smaller by making the expansion height of the second protrusion towards the skin side lower than the expansion height of the first protrusion towards the skin side, by making the area of the planar shape of the second protrusion smaller than the area of the planar shape of the first protrusion, or by both of the above.

As the present invention according to claim 4, the absorbent article according to claim 1, wherein the weight per unit area of the highly water-absorbent polymer filled into the first space parts is 50 to 300 g/m$^2$, and the weight per unit area of the highly water-absorbent polymer filled into the second space parts is 20 to 150 g/m$^2$, is provided.

In the invention of the above-described claim 4, the weight per unit area of the highly water-absorbent polymer filled into first space parts and the weight per unit area of the highly water-absorbent polymer filled into second space parts are defined specifically.

As the present invention according to claim 5, the absorbent article according to claim 1, wherein a volume ratio of the first space part:the second space part is 2 to 10:1, is provided.

In the invention of the above-described claim 5, the volume ratio of the first space part to the second space part is defined specifically.

As the present invention according to claim 6, the absorbent article according to claim 1, wherein the first protrusions and the second protrusions are arranged alternately in a grid shape, is provided.

In the invention of the above-described claim 6, the first protrusions and the second protrusions are arranged alternately in a grid shape, and therefore, the front, back, right and left sides of the second protrusion are surrounded by the first protrusions, and the second protrusions adjoining in an oblique direction are arranged continuously with each other. Accordingly, it becomes easier for the body fluid to diffuse along the adjacent second protrusions in an oblique direction.

As the present invention according to claim 7, the absorbent article according to claim 1, wherein the planar shape of the first protrusion is a circular shape or an elliptic shape and the first protrusions are arranged in a grid shape, and areas of which its four corners are surrounded by the first protrusions are the second protrusions, is provided.

In the invention of the above-described claim 7, the first protrusions wherein its planar shape is a circular shape or an elliptic shape are arranged in a grid shape, and areas of which its four corners are surrounded by the first protrusions, in other words, areas of which its surroundings are partitioned at its four corners by quadrant parts of the first protrusions, are the second protrusions. Accordingly, the second space part within the second protrusion has a relatively smaller volume, and it becomes easier for the body fluid to diffuse along the second space parts.

As the present invention according to claim 8, the absorbent article according to claim 1, wherein each of outer peripheries of the first protrusions and the second protrusions is a joining part with the lower layer sheet, and the joining parts of the adjacent first protrusions or the second protrusions are provided continuously, is provided.

In the invention of the above-described claim 8, a joining part with the lower layer sheet is provided at each outer periphery of the first protrusions and the second protrusions, and the joining parts of the adjacent first protrusions or the second protrusions are provided continuously. Accordingly, a flow of the body fluid occurs along the joining parts, and it becomes possible to improve the diffusibility of the body fluid. In this connection, the phrase "the joining parts of the adjacent first protrusions or the second protrusions are provided continuously" means that portions of adjacent joining parts, which are formed either at the outer peripheries of two first protrusions, the outer peripheries of two second protrusions, or the outer peripheries of a first protrusion and a second protrusion, overlap or connect, and that the height of the joining parts at the skin side surface are formed to be approximately the same in these connected parts.

As the present invention according to claim 9, the absorbent article according to claim 1, wherein a fiber assembly layer including a water-absorbing fiber assembly is arranged on the non-skin side or the skin side of the absorbing body, is provided.

In the invention of the above-described claim 9, by combining the absorbing body with the fiber assembly layer, the absorbability of the body fluid is enhanced furthermore.

Advantageous Effects of Invention

As described in detail above, according to the present invention, improvement of the diffusibility of body fluid and enhancement of the capability of quickly absorbing body fluid are enabled.

DESCRIPTION OF EMBODIMENTS

Embodiments of the present invention are described in detail hereinbelow referring to the drawings.

[Basic Construction of Sanitary Napkin 1]

Figure 1:
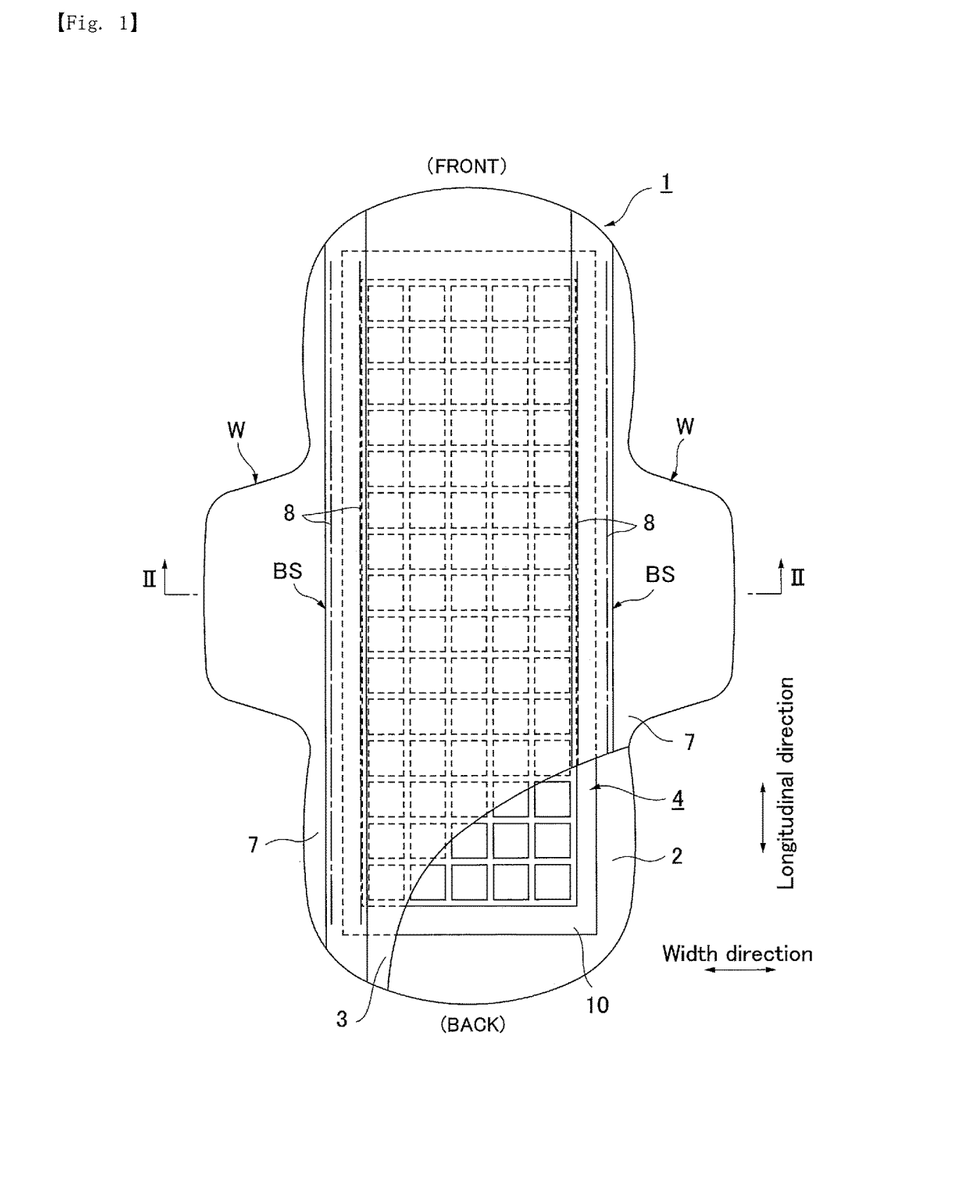
FIG. 1 is a partially cutaway expansion view of a sanitary napkin 1 according to the present invention.
Figure 2:
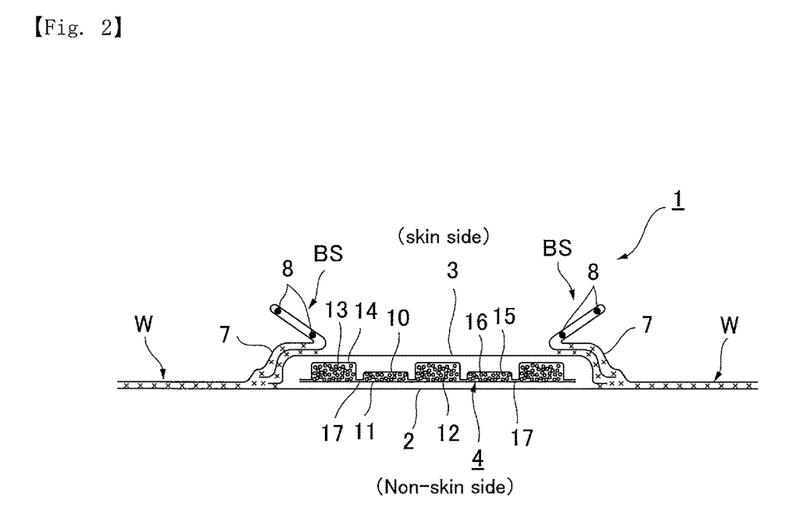
FIG. 2 is an arrow view taken along the II-II line of FIG. 1.

A sanitary napkin 1 according to the present invention is composed of a liquid impermeable rear surface sheet 2 formed of a polyethylene sheet, a polypropylene sheet, and the like, a liquid permeable front surface sheet 3 which makes menstrual blood, vaginal discharge, and the like permeate quickly, an absorbing body 4 which is provided between these sheets 2 and 3 and has a structure where a highly water-absorbent polymer is interposed between two layers of sheets, and side nonwoven fabrics 7 and 7 provided along the longitudinal direction on both side parts of the surface-side, respectively, as shown in FIGS. 1 and 2. In addition, at the periphery of the absorbing body 4, at the front and back end edges in the longitudinal direction of the napkin, the outer edges of the liquid impermeable rear surface sheet 2 and the liquid permeable front surface sheet 3 are joined together by an adhesion means such as an adhesive including a hot-melt adhesive and heat sealing. In addition, at both side edges of the napkin, the liquid impermeable rear surface sheet 2 which extends further outward than the side edges of the absorbing body 4 and the side nonwoven fabric 7 are joined together by an adhesion means such as an adhesive including a hot-melt adhesive and heat sealing. Accordingly, an outer periphery flap part in which the absorbing body 4 is not present is formed at the outer periphery.

The structure of the sanitary napkin 1 is further described in more detail hereinbelow.

As the liquid impermeable rear surface sheet 2, a sheet material having at least water imperviousness, such as an olefin-based resin sheet including polyethylene and polypropylene, is used. Besides the above, laminated nonwoven fabric in which nonwoven fabric is laminated on a polyethylene sheet and the like, or a nonwoven fabric sheet in which liquid impermeability is substantially secured by intervention of a waterproof film (in this case, the liquid impermeable rear surface sheet is composed of the waterproof film and a nonwoven fabric) and the like may be used. In recent years, materials having moisture permeability tend to be used from the aspect of preventing mustiness. The water impervious and moisture permeable sheet material is a microporous sheet which can be obtained by a method which comprises molding a sheet by melt-kneading olefin based resin such as polyethylene and polypropylene with an inorganic filler, and stretching the sheet monoaxially or diaxially.

Next, as the liquid permeable front surface sheet 3, a porous or nonporous nonwoven fabric, a porous plastic sheet and the like are suitably used. As the material fiber constituting the nonwoven fabric, synthetic fiber such as olefin based fiber including polyethylene and polypropylene, polyester based fiber, and polyamide based fiber, regenerated fiber such as rayon and cupra, as well as natural fiber such as cotton may be used, for example. Nonwoven fabric obtained by appropriate processing methods such as the spunlace method, the spunbond method, the thermal bonding method, the melt blowing method, and the needle punch method may be used. Among these processing methods, the spunlace method excels in view of providing flexibility, the spunbond method excels in view of providing draping property, and the thermal bonding method and the air-through method excel in view of providing bulk and high compression restorability. The liquid permeable front surface sheet 3 may not be provided in the case where the upper layer sheet 10 of the absorbing body 4 constitutes a skin-abutting surface layer described in detail hereinbelow.

The absorbing body 4 which is interposed between the liquid impermeable rear surface sheet 2 and the liquid permeable front surface sheet 3 has a structure wherein a highly water-absorbent polymer 12 is interposed between an upper layer sheet 10 disposed on the skin side and a lower layer sheet 11 disposed on the non-skin side.

As the upper layer sheet 10, porous or nonporous nonwoven fabric and porous plastic sheets are used. As the material fiber which constitutes the nonwoven fabric, as with the liquid permeable front surface sheet 3, synthetic fiber such as olefin based fiber including polyethylene and polypropylene, polyester based fiber, and polyamide based fiber, regenerated fiber such as rayon and cupra, as well as natural fiber such as cotton may be used, for example. The processing method of the nonwoven fabric is not limited, but processing methods such as the spunbond method, the melt blowing method, and the needle punch method, all of which elevate the fiber density of the obtained product, are preferable in order to prevent the highly water-absorbent polymer 12 from falling out. The pore diameter of the porous plastic sheet is preferably smaller than the outside diameter of the highly water-absorbent polymer 12 in order to prevent the highly water-absorbent polymer 12 from falling out. In addition, as described in detail hereinbelow, the upper layer sheet 10 preferably contains a material having thermoplasticity, since the upper layer sheet 10 is subjected to a predetermined concavo-convex processing.

As the lower layer sheet 11, porous or nonporous nonwoven fabric, a porous plastic sheet may be used, as well as a sheet material having water imperviousness. As is the case with the upper layer sheet 10, the processing method of the nonwoven fabric is not limited, but processing methods such as the spunbond method, the melt blowing method and the needle punch method, all of which elevate the fiber density of the obtained product, is preferable in order to prevent the highly water-absorbent polymer 12 from falling out. The pore diameter of the porous plastic sheet is preferably smaller than the outside diameter of the highly water-absorbent polymer 12 in order to prevent the highly water-absorbent polymer 12 from falling out. As the sheet material having water imperviousness, the same material as that of the liquid impermeable rear surface sheet 2 may be used.

Examples of the highly water-absorbent polymer 12 include a polyacrylate cross-linked product, a self-crosslinking polyacrylate, a saponified product of an acrylic ester-vinyl acetate copolymer cross-linked product, an isobutylene-maleic anhydride copolymer cross-linked product, a polysulfonate cross-linked product, a product obtained by partially crosslinking a water-swelling polymer such as a polyethylene oxide and a polyacrylamide, and the like. Among them, an acrylic acid based product and an acrylate based product are suitable because they excel in the amount and speed of water absorption. The water-absorbing capacity and speed of the highly water-absorbent polymer having said water absorption performance can be adjusted during the manufacturing process by adjusting the crosslinking density and the crosslinking density gradient.

Meanwhile, side nonwoven fabrics 7 and 7 are provided at both side parts of the surface-side of the present sanitary napkin 1, respectively, along the longitudinal direction and substantially over the whole length of the napkin 1. A part of each of these side nonwoven fabrics 7 and 7 is extended to the side of the napkin 1, and together with a part of the liquid impermeable rear surface sheet 2 which is extended to the side of the napkin 1 likewise, forms wing-like flaps W and W.

As the side nonwoven fabric 7, a nonwoven fabric subjected to a water repellent treatment or a nonwoven fabric subjected to a hydrophilic treatment may be used, depending on the functions regarded as important. For example, if the function of preventing menstrual blood, vaginal discharge and the like from permeating or the function of improving the texture are regarded as important, it is desirable to use a nonwoven fabric subjected to a water repellent treatment wherein the fabric is coated with a silicon based water repellent, a paraffin based water repellent, an alkylchromic chloride based water repellent, or the like. In addition, if the absorbability of menstrual blood and the like in the wing-like flaps W and W is regarded as important, it is desirable to use a nonwoven fabric subjected to a hydrophilic treatment, wherein the hydrophilicity is provided by making synthetic fiber swollen or porous by applying capillary phenomenon, using, for example, a method which comprises conducting polymerization by making a compound having a hydrophilic group, such as an oxidation product of a polyethylene glycol, coexist in the process of manufacturing the synthetic fiber, or a method which comprises treating the synthetic fiber with a metal salt such as stannic chloride so that the surface is partially dissolved to be porous and depositing a hydroxide of a metal.

With regards to the inner part of the side nonwoven fabric 7, as shown in FIG. 2, the side nonwoven fabric 7 is almost doubly folded, and inside the doubly folded sheet, one or a plurality of—two in the illustrated example—yarn-like elastic expansion and contraction members 8 and 8 of which the both ends or the appropriate positions in the longitudinal direction are fixed at the middle part in the height direction of the doubly folded sheet, are provided. Owing to the contractive force of the two yarn-like elastic expansion and contraction members 8, three-dimensional gathers BS and BS are formed by making the doubly folded sheet part erect towards the skin side.

[Absorbing Body 4]

Figure 3:
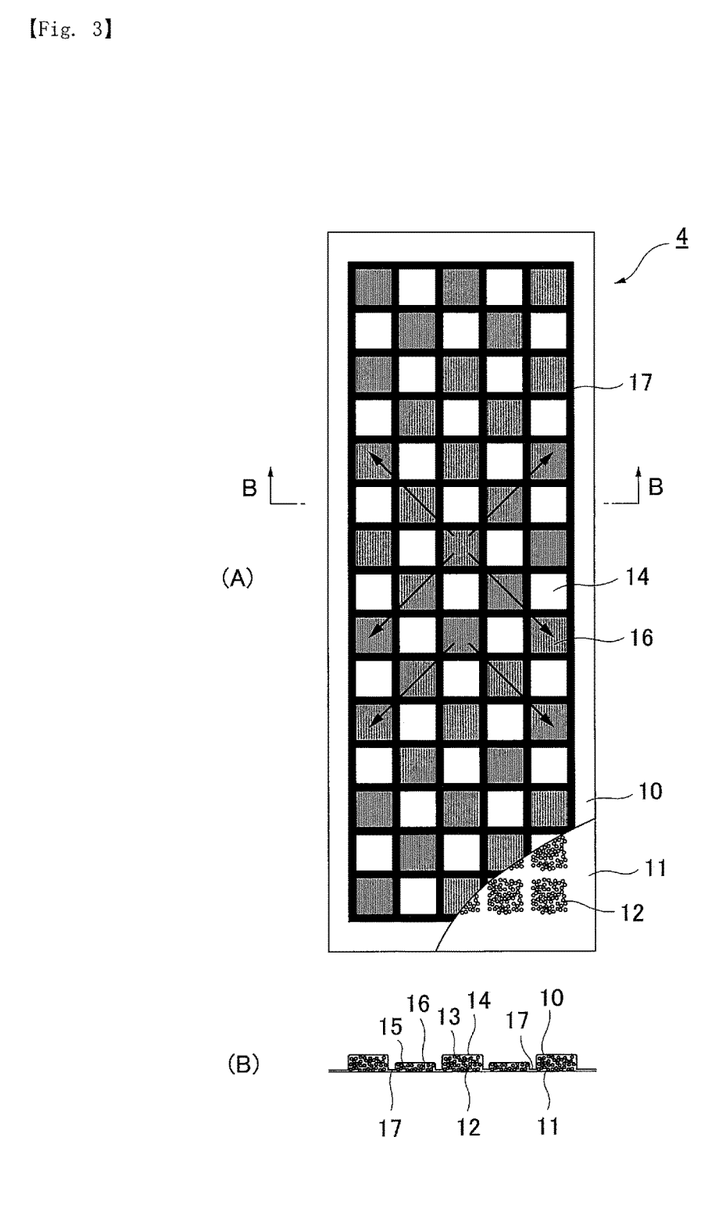
FIG. 3(A) is a plan view of an absorbing body 4.
FIG. 3(B) is an arrow view taken along the B-B line of FIG. 3(A).

The absorbing body 4 is described in detail hereinbelow. The absorbing body 4 has a structure in which the highly water-absorbent polymer 12 is interposed between the upper layer sheet 10 disposed on the skin side (on the side of the liquid permeable front surface sheet 3) and the lower layer sheet 11 disposed on the non-skin side (on the side of the liquid impermeable rear surface sheet 2), as shown in FIGS. 1 to 3.

The upper layer sheet 10 has a plurality of first protrusions 14 forming first space parts 13 that are to be filled with the highly water-absorbent polymer 12 and that expand to the skin side, and a plurality of second protrusions 16 forming second space parts 15, each of which having a smaller volume than each of the first space parts 13, that are to be filled with the highly water-absorbent polymer 12 and that expand to the skin side. The upper layer sheet 10 is formed into a concavo-convex shape in which numerous first protrusions 14, 14 . . . and second protrusions 16, 16 . . . that expand to the skin side are formed. On the other hand, the lower layer sheet 11 is formed into a flat surface shape. Accordingly, the first space parts 13 are formed inside the first protrusions 14 and the second space parts 15 are formed inside the second protrusions 16, between the upper layer sheet 10 and the lower layer sheet 11, in a state where the lower layer sheet 11 is laminated on the non-skin side of the upper layer sheet 10. Each of these first space parts 13 and second space parts 15 accommodates a predetermined amount of the highly water-absorbent polymer 12.

The second space part 15 has a smaller volume than the first space part 13. The volume of the first space part 13 means the volume of the space partitioned by the upper layer sheet 10 and the lower layer sheet 11 within the first protrusion 14 that expands to the skin side. In addition, the volume of the second space part 15 means the volume of the space partitioned by the upper layer sheet 10 and the lower layer sheet 11 within the second protrusion 16 that expands to the skin side. In order to make the second space part 15 have a smaller volume than the first space part 13, when the first protrusion 14 and the second protrusion 16 are formed to have the same planar shape (area) as shown in FIG. 3(A), the expansion height of the second protrusion 16 towards the skin side may be made lower than the expansion height of the first protrusion 14 towards the skin side, as shown in FIG. 3(B). On the other hand, when the second protrusion 16 is formed to have a smaller planar shape (area) than the first protrusion 14, the second space part 15 is capable of having a smaller volume than the first space part 13, by making the expansion height of the first protrusion 14 towards the skin side and the expansion height of the second protrusion 16 towards the skin side the same, or by making the expansion height of the second protrusion 16 relatively lower than that of the first protrusion 14 (see FIG. 7).

The weight per unit area of the highly water-absorbent polymer 12 filled into the second space parts 15 is set to be smaller than the weight per unit area of the highly water-absorbent polymer 12 filled into the first space parts 13. In other words, the second space parts 15 accommodate a relatively smaller amount of the highly water-absorbent polymer 12 than the first space parts 13. Specifically, the weight of the highly water-absorbent polymer 12 filled into the first space parts 13 is 50 to 300 $g/m^2$, preferably 100 to 200 $g/m^2$, and the weight of the highly water-absorbent polymer 12 filled into the second space parts 15 is 20 to 150 $g/m^2$, preferably 30 to 100 $g/m^2$.

As described above, in the absorbing body 4, numerous first protrusions 14 and second protrusions 16, both having different internal volumes, are formed, and therefore, it becomes easier for the body fluid to diffuse along the boundary portions between the first protrusions 14 and the second protrusions 16. Accordingly, the body fluid can be quickly absorbed by a large area of the highly water-absorbent polymer 12. Further, in addition to making the second space parts 15 have smaller volumes than the first space part 13, the weight per unit area of the highly water-absorbent polymer 12 filled into the second space parts 15 is made smaller than the weight per unit area of the highly water-absorbent polymer 12 filled into the first space parts 13. Accordingly, when the planar shape of the first protrusion 14 and that of the second protrusion 16 are the same, the second protrusion 16 has a lower expansion height towards the skin side than the first protrusion 14, and therefore, it becomes easier for the body fluid to diffuse along the second protrusions 16 which have lower heights. In addition, when the planar shape of the second protrusion 16 is made smaller than that of the first protrusion 14, it becomes easier for the body fluid to diffuse along the second protrusions 16 which have smaller planar shapes. As such, it becomes easier for the body fluid to diffuse along the second protrusions 16 which have relatively smaller volumes, and therefore, the body fluid can be quickly absorbed by the highly water-absorbent polymer 12 having a large area.

With regards to the volume ratio between the first space parts 13 and the second space parts 15, it is preferable that it would be as below, specifically: the first space parts 13:the second space parts 15=2 to 10:1. In other words, the volume of the second space parts 15 is preferably about ½ to ⅒ of the volume of the first space parts 13. Owing to this ratio, each of the second space parts 15 has a sufficiently smaller volume than each of the first space parts 13, and it becomes easier for the body fluid to diffuse along the second protrusions 16.

The filling rate of the highly water-absorbent polymer 12 filled into the first space parts 13 and the second space parts 15 (the ratio of the volume of the accommodated highly water-absorbent polymer 12 vis-a-vis the volume of each of space parts 13 and 15) is preferably about equal to or higher than 10% and about equal to or lower than 70%. When the filling rate is lower than 10%, the highly water-absorbent polymer 12 has smaller chance to come in contact with the body fluid, and therefore, the body fluid cannot be absorbed quickly. When the filling rate is higher than 70%, the space parts tend to expand too much when the napkin absorbs water and swells, and reversion of the body fluid may occur. The filling rate with regards to the first space parts 13 and that with regards to the second space parts 15 may be the same or different from each other. For example, the filling rate with regards to second space parts 15 may be made smaller than the filling rate with regards to first space parts 13, in order to achieve quick absorption of the body fluid in the second space parts 15 and to secure a sufficient absorption capacity in the first space parts 13.

The planar shape of each of the first protrusions 14 and the second protrusions 16 may be a square or a rectangle as shown in FIG. 3, and the first protrusions 14 and the second protrusions 16 may be arranged alternately in a grid shape such that they form a checkered pattern as a whole. Owing to such an arrangement, the body fluid diffuses in an oblique direction along the second protrusions 16.

Figure 7:
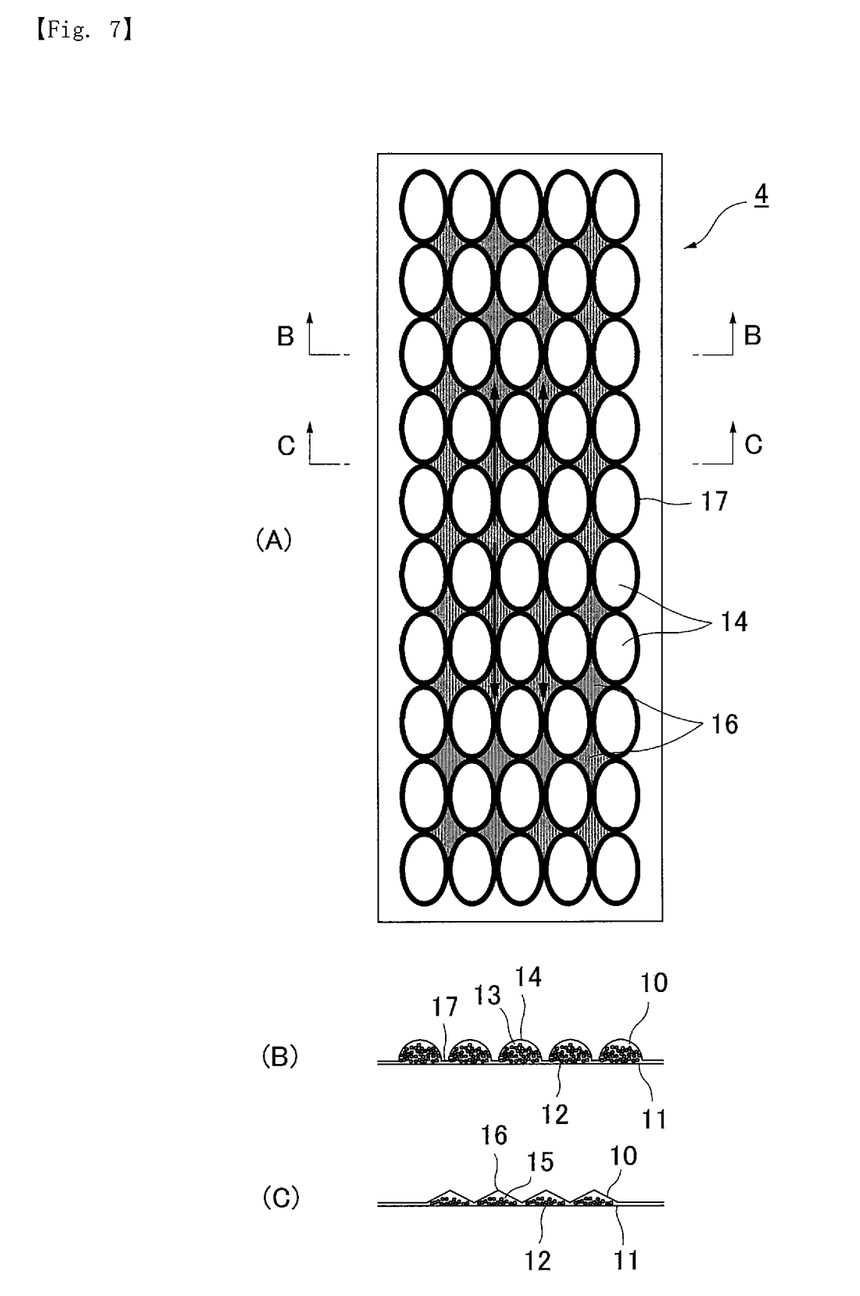
FIG. 7(A) is a plan view which show an absorbing body 4 according to another embodiment.
FIG. 7(B) is an arrow view taken along the B-B line of FIG. 7(A)
FIG. 7(C) is an arrow view taken along the C-C line of FIG. 7(A).

The cross-sectional shape of each of the first protrusions 14 and the second protrusions 16 may be a rectangular cross sectional shape having an almost flat surface as shown in FIG. 3, a curved cross section which expands to the skin side in a dome shape, or a conical cross section which forma linear slope toward the skin side (see FIG. 7). In addition, the cross-sectional shape of the first protrusion 14 and that of the second protrusion 16 may be the same or different from each other. It is preferable that the first protrusion 14 has a cross-sectional shape having a flat top part such that a greater amount of the highly water-absorbent polymer 12 can be accommodated within the first space part 13. Meanwhile, it is preferable that the second protrusion 16 has a conical cross section with its top part being narrow such that a relatively smaller amount of the highly water-absorbent polymer 12 is accommodated within the second space part 15.

A plurality of the first protrusions 14, 14 . . . are arranged around the second protrusion 16, and it is preferable that a part in which the first protrusions 14 do not intervene is provided between the adjacent second protrusions 16 and 16. In other words, in an example shown in FIG. 3, first protrusions 14, 14 . . . are arranged at both sides of one second protrusion 16 in the longitudinal direction and the width direction, respectively, such that the first protrusions 14, 14 . . . adjoin the second protrusion 16. At the same time, the second protrusion 16 is arranged to adjoin the second protrusion 16 in an oblique direction, and between the adjacent second protrusions 16 and 16, a part in which the first protrusions 14 do not intervene is provided. Owing to such an arrangement, it becomes easier for the body fluid to diffuse in an oblique direction along the adjacent second protrusions 16 and 16 via the parts in which the first protrusions 14 do not intervene.

Each of outer peripheries of the first protrusions 14 and the second protrusions 16 is a joining part 17 with the lower layer sheet 11. The joining part 17 is provided such that it surrounds the outer peripheries of the first protrusions 14 and the second protrusions 16, and the upper layer sheet 10 and the lower layer sheet 11 are joined together continuously or intermittently in the circumferential direction. As for the joining part 17, a known joining means such as heat sealing, ultrasonic wave, and adhesives may be employed. However, the use of adhesives is not preferable because the highly water-absorbent polymer 12 may enter the joining part between the upper layer sheet 10 and the lower layer sheet 11 such that the bonding strength decreases. Therefore, it is preferable to use heat sealing or an ultrasonic wave.

It is preferable that the joining parts 17 provided at the outer peripheries of the first protrusions 14 and the second protrusions 16 are arranged such that the adjacent joining parts 17, 17 . . . are provided continuously. Owing to such an arrangement, it becomes easier for the body fluid to flow along the joining parts 17, and the diffusibility of the body fluid improves. In an example shown in FIG. 3(A), the continuous grid shaped joining parts 17 are provided over almost the entire surface of the absorbing body 4. Meanwhile, at the joining part 17, the upper layer sheet 10 is either consolidated or applied with a water-impermeable adhesive, and therefore, the effect that enables the body fluid to permeate becomes extremely low, while the diffusibility of the body fluid becomes excellent. The body fluid diffused in such a manner permeates into a larger area of the first protrusions 14 or the second protrusions 16 and is absorbed quickly by the highly water-absorbent polymer 12 inside the first protrusions 14 or the second protrusions 16.

It is preferable that the first protrusions 14 and the second protrusions 16 are formed in an intermediate region which does not reach end parts of the upper layer sheet 10 and the lower layer sheet 11 in the longitudinal direction and the width direction in order to prevent the highly water-absorbent polymer 12 accommodated inside the first protrusions 14 and the second protrusions 16 from falling out from the edges. At the edges of the upper layer sheet 10 and the lower layer sheet 11, the upper layer sheet 10 and the lower layer sheet 11, which are located further on the external edges with regards to the joining parts 17 of the first protrusions 14 and the second protrusions 16, may not be joined together, but it is preferable that the upper layer sheet 10 and the lower layer sheet 11 are joined by a joining means such as adhesives, heat sealing, and ultrasonic wave in order to prevent the highly water-absorbent polymer 12 accommodated in the sanitary napkin from falling out during manufacturing or use of the sanitary napkin.

Figure 4:
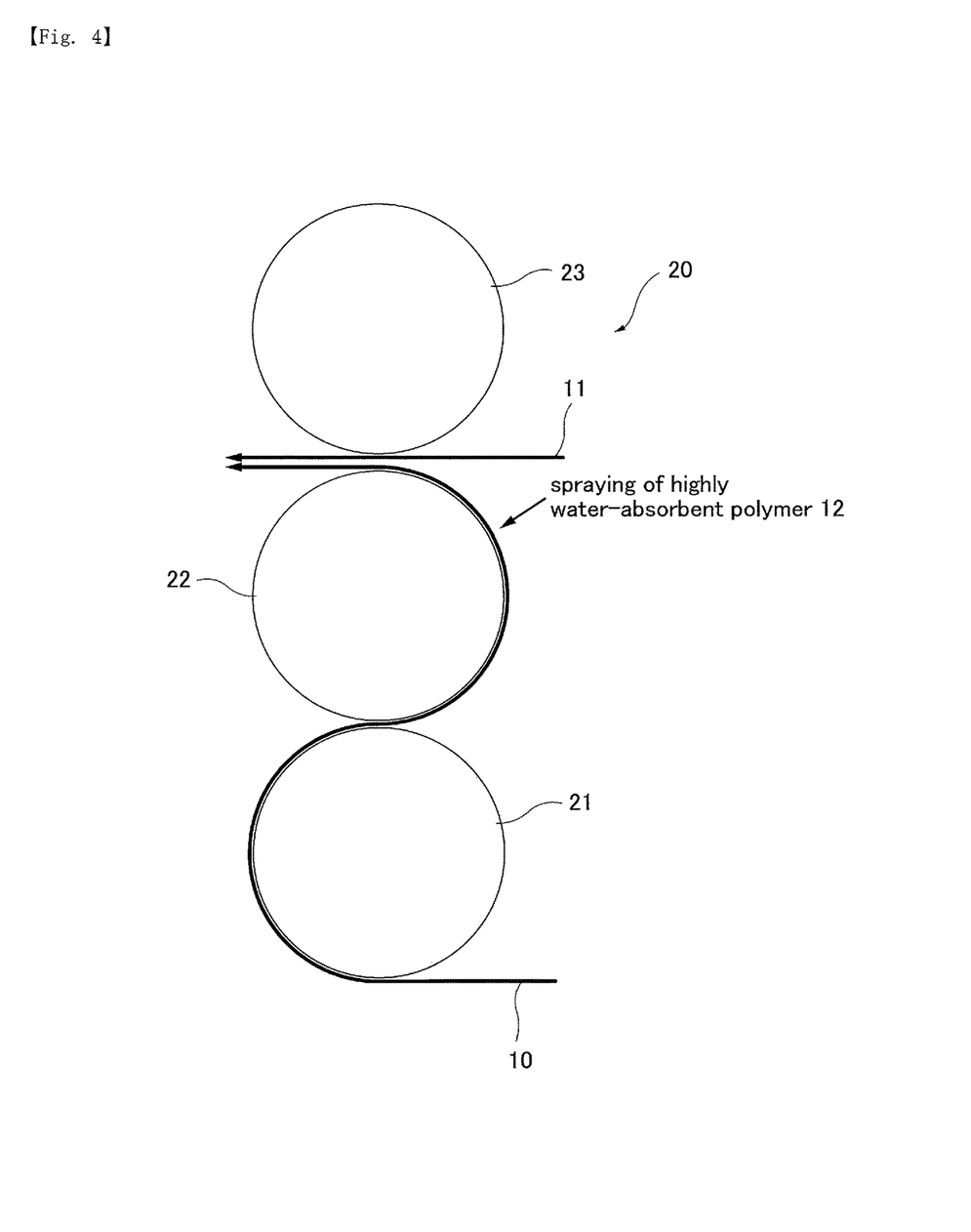
FIG. 4 is a side view which shows a manufacturing apparatus 20 of an absorbing body 4.
Figure 5:
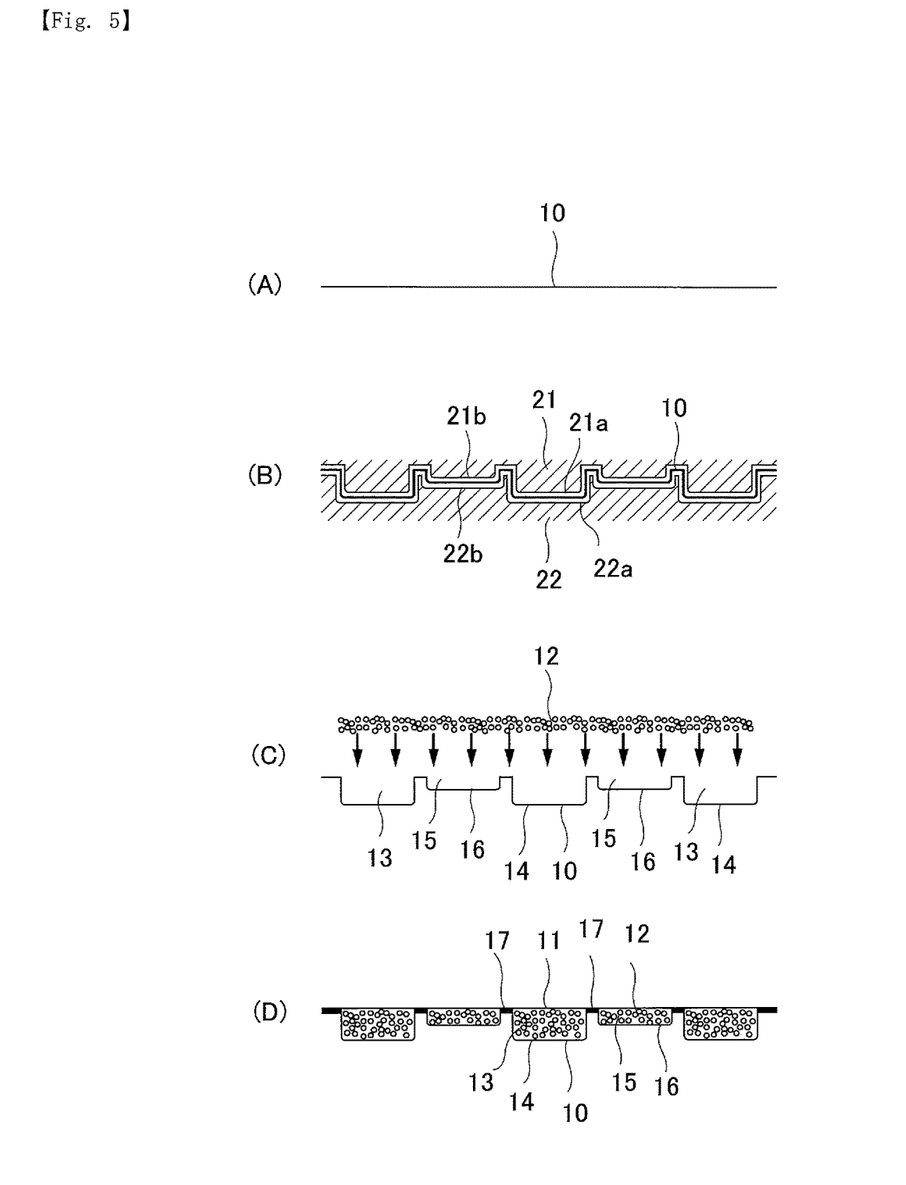
FIGS. 5(A) to 5(D) are cross-sectional views which show a manufacturing procedure of an absorbing body 4.

For the manufacturing of the absorbing body 4, as shown in FIGS. 4 and 5, it is preferable to use a manufacturing apparatus 20 which makes the upper layer sheet 10 pass between a first embossing roll 21, on which numerous convexes 21a, 21a . . . corresponding to the first protrusions 14 and numerous convexes 21b, 21b . . . corresponding to the second protrusions 16 are arranged, and a second embossing roll 22, on which numerous concaves 22a, 22a . . . corresponding to the convexes 21a and numerous concaves 22b, 22b . . . corresponding to the convexes 21b are arranged, such that the first protrusions 14 are formed by the meshing of the convexes 21a and the concaves 22a and that the second protrusions 16 are formed by the meshing of the convexes 21b and the concaves 22b.

Thereafter, the highly water-absorbent polymer 12 is sprayed on the surface of the second embossing roll 22 on which the upper layer sheet 10 is disposed, and thus the highly water-absorbent polymer 12 is accommodated within the concaves, and the lower layer sheet 11 transported from another pathway is passed between the second embossing roll 22 and a flat roll 23 in a state in which the lower layer sheet 11 is laminated, so that the upper layer sheet 10 and the lower layer sheet 11 are joined and integrated. For the joining, a hot-melt adhesive or the like may be applied beforehand on the outer surface of the upper layer sheet 10 which corresponds to convexes of the second embossing roll 22, and then the upper layer sheet 10 and the lower layer sheet 11 may be adhered to each other. Otherwise, the upper layer sheet 10 and the lower layer sheet 11 may be fused together by heating the convexes of the second embossing roll 22 or irradiating an ultrasonic wave onto the convexes of the second embossing roll 22 at the time of the meshing of the second embossing roll 22 and the flat roll 23.

By providing suction openings on the bottom of the concaves 22a and 22b of the second embossing roll 22, the embossing is facilitated by suctioning the upper layer sheet 10 at the time of embossing, and to prevent the highly water-absorbent polymer 12 from falling out during the spraying of the highly water-absorbent polymer 12 with the suctioning. In addition, after the highly water-absorbent polymer 12 is sprayed, the amount of the highly water-absorbent polymer 12 accommodated within the first space parts 13 and the second space parts 15 may be adjusted by flattening the surface with a scraper or the like.

Figure 6:
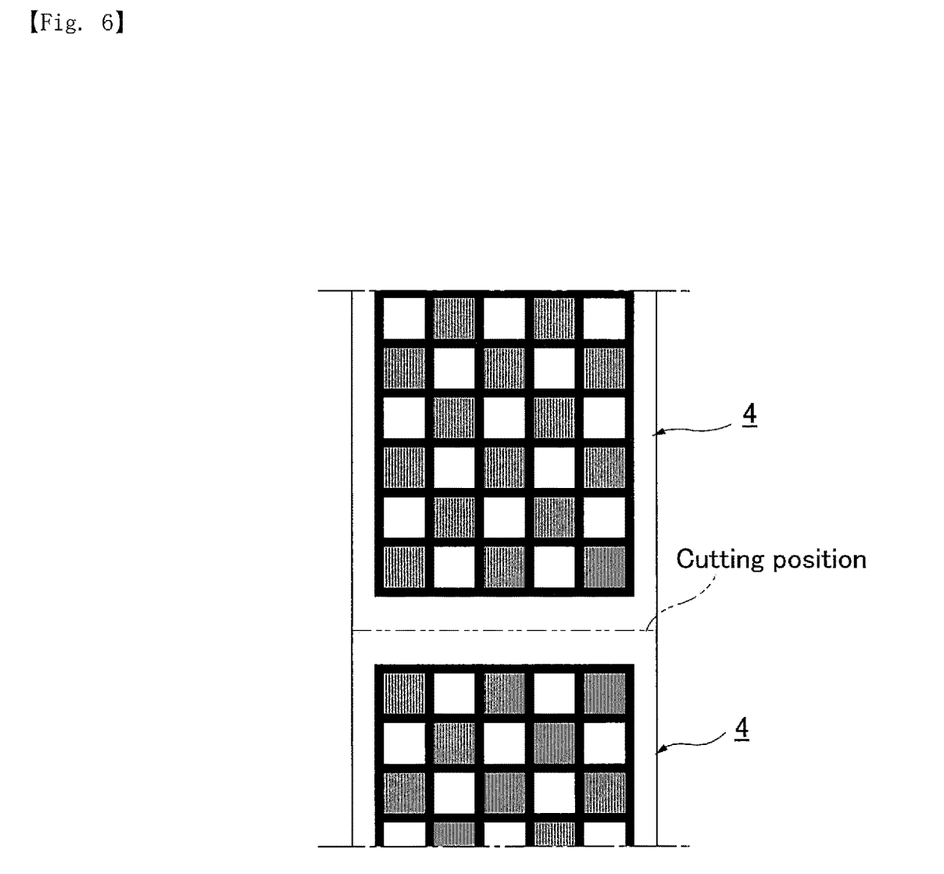
FIG. 6 is a plan view which shows a cutting position of continuous absorbing bodies 4 and 4.

After that, as shown in FIG. 6, the absorbing bodies 4, 4 . . . which continue in the longitudinal direction are cut at the joining part of the upper layer sheet 10 and the lower layer sheet 11 wherein neither of the first protrusions 14 nor the second protrusions 16 are formed.

Next, variations of the absorbing body 4 are described. In order to make the volume of the second space part 15 smaller than the volume of the first space part 13, as shown in FIG. 3, under the condition that the planar shape (area) of the first protrusion 14 and that of the second protrusion 16 are the same, the expansion height of the second protrusion 16 towards the skin side is made lower than the expansion height of the first protrusion 14 towards the skin side. Otherwise, as shown in FIG. 7, under the condition that the area of the planar shape of the second protrusion 16 is smaller than the area of the planar shape of the first protrusion 14, the volume of the second space part 15 is made smaller than the volume of the first space part 13 by making the expansion height of the first protrusion 14 towards the skin side and that of the second protrusion 16 towards the skin side the same, or by making the expansion height of the second protrusion 16 towards the skin side relatively smaller than that of the first protrusion 14 towards the skin side.

In an example shown in FIG. 7, first protrusions 14 having a circular or elliptic planar shape, which is an elliptic shape that is long in the longitudinal direction of the napkin in the illustrated example, are arranged in a grid shape, and areas of which the four corners are surrounded by the first protrusions 14, 14 . . . are designated as the second protrusions 16. It is preferable that the cross-sectional shape of the first protrusion 14 is, as shown in FIG. 7(B), formed in a dome shape, and that the cross-sectional shape of the second protrusion 16 is, as shown in FIG. 7(C), formed in a conical shape. Owing to this, it becomes easier for the body fluid to diffuse along the second protrusions 16.

When the first protrusions 14 and the second protrusions 16 are arranged in the form of FIG. 7, as shown in FIG. 7(A), it is preferable that the planar shape of the first protrusion 14 is an elliptic shape which is long in the longitudinal direction of the napkin. Owing to this, the respective second protrusions 16, each of which its four corners are surrounded by the first protrusions 14, is formed in a planar shape which is long in the longitudinal direction of the napkin, and therefore, it becomes possible for the body fluid to be diffused along the second protrusions 16 in the longitudinal direction of the napkin, and the side leak of the body fluid can be prevented.

Figure 8:
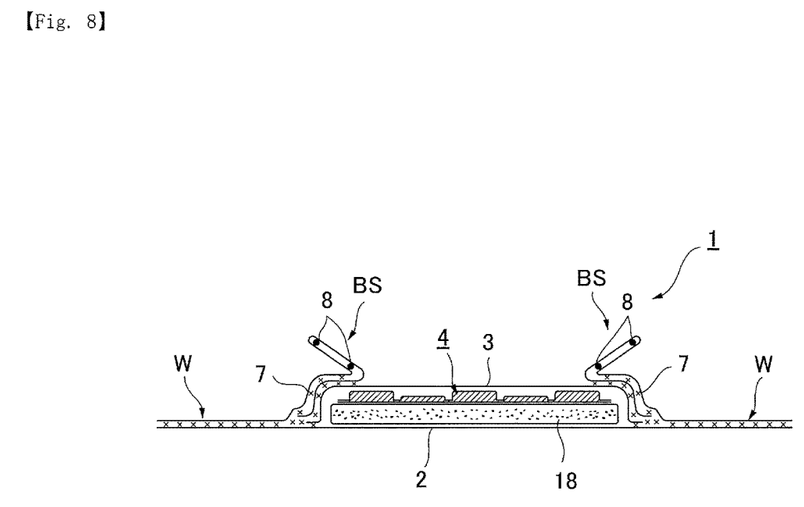
FIG. 8 is a cross-sectional view (part 1) of a sanitary napkin 1 according to another embodiment.
Figure 9:
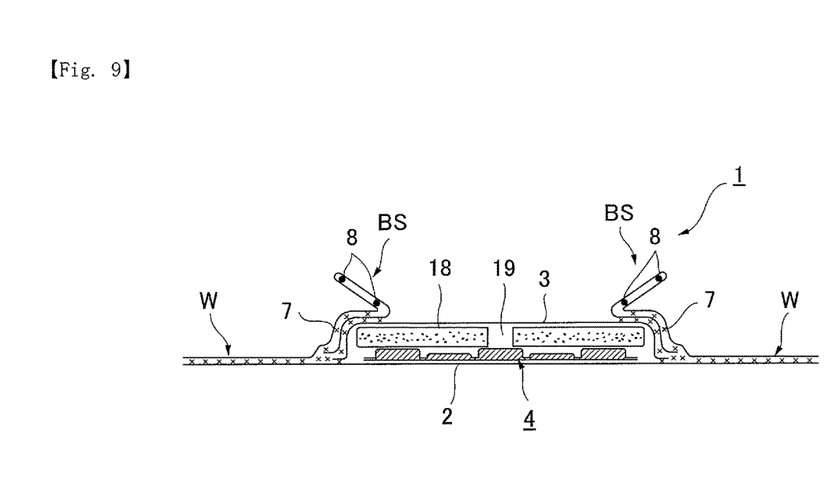
FIG. 9 is a cross-sectional view (part 2) of a sanitary napkin 1 according to another embodiment.

The absorbing body 4 may be singly interposed between the liquid permeable front surface sheet 3 and the liquid impermeable rear surface sheet 2, as shown in FIG. 2. The absorbing body 4 may also be disposed as a laminate with a fiber assembly layer 18 which includes an assembly of water-absorbing fiber such as pulp disposed on the non-skin side or the skin side of the absorbing body 4, as shown in FIGS. 8 and 9. The fiber assembly layer 18 is composed of at least a water-absorbing fiber assembly, and may be mixed with a highly water-absorbent polymer.

In FIG. 8, the fiber assembly layer 18 is disposed on the non-skin side of the absorbing body 4, and a laminate of the absorbing body 4 and the fiber assembly layer 18 is interposed between the liquid permeable front surface sheet 3 and the liquid impermeable rear surface sheet 2. Owing to this, the body fluid which has permeated the absorbing body 4 which is the upper layer can be absorbed and retained by the fiber assembly layer 18 which is the lower layer. In this case, it is preferable to use a water-permeable sheet material as the lower layer sheet 11 which constitutes the absorbing body 4.

In FIG. 9, the fiber assembly layer 18 is disposed on the skin side of the absorbing body 4, and a laminate of the absorbing body 4 and the fiber assembly layer 18 is interposed between the liquid permeable front surface sheet 3 and the liquid impermeable rear surface sheet 2. Owing to this, the body fluid which has diffused in the fiber assembly layer 18 can be quickly absorbed by the absorbing body 4. In this case, as shown in FIG. 9, a slit 19 which goes through along the longitudinal direction in the central part in the width direction of the fiber assembly layer 18 may be provided. Owing to this, the slit 19 acts as a temporarily storing space of the body fluid, and then the body fluid can diffuse in the longitudinal direction along the slit 19, and simultaneously along the second protrusions 16 on the surface of the absorbing body 4. Accordingly, it becomes possible that the napkin is excellent in the diffusibility and that the body fluid is efficiently and quickly absorbed by the absorbing body 4.

When a laminate of the absorbing body 4 and the fiber assembly layer 18 is used, the absorbing body 4 is not required to be disposed on the whole surface of the fiber assembly layer 18, and for example, the absorbing body 4 may be disposed only in the center region of the napkin including the blood outlet, or may be disposed only in the annular region surrounding the blood outlet. In this case, the fiber assembly layer 18 is arranged up to the outer periphery part of the sanitary napkin 1, except for the outer periphery flap part.

In addition, though not illustrated, the liquid permeable front surface sheet 3 is not necessarily an essential component, and in the case where the upper layer sheet 10 of the absorbing body 4 acts as the skin abutting surface layer, the liquid permeable front surface sheet 3 is not required to be disposed. Owing to this, the sanitary napkin 1 can be made even thinner, and the cost can be reduced thanks to the decrease in the number of materials.

Other Embodiments (1) In the above-described embodiment, two kinds of protrusions, which are the first protrusions 14 forming the first space parts 13 and the second protrusions 16 forming the second space parts 15, each of which having a relatively smaller volume than each of the first space parts 13, are provided, but additionally, further protrusions forming space parts, each of which having a relatively smaller volume than the second space part 15, may be provided. Owing to this, the body fluid diffuses through the protrusions, and the diffusibility of the body fluid further more improves.

Figure 10:
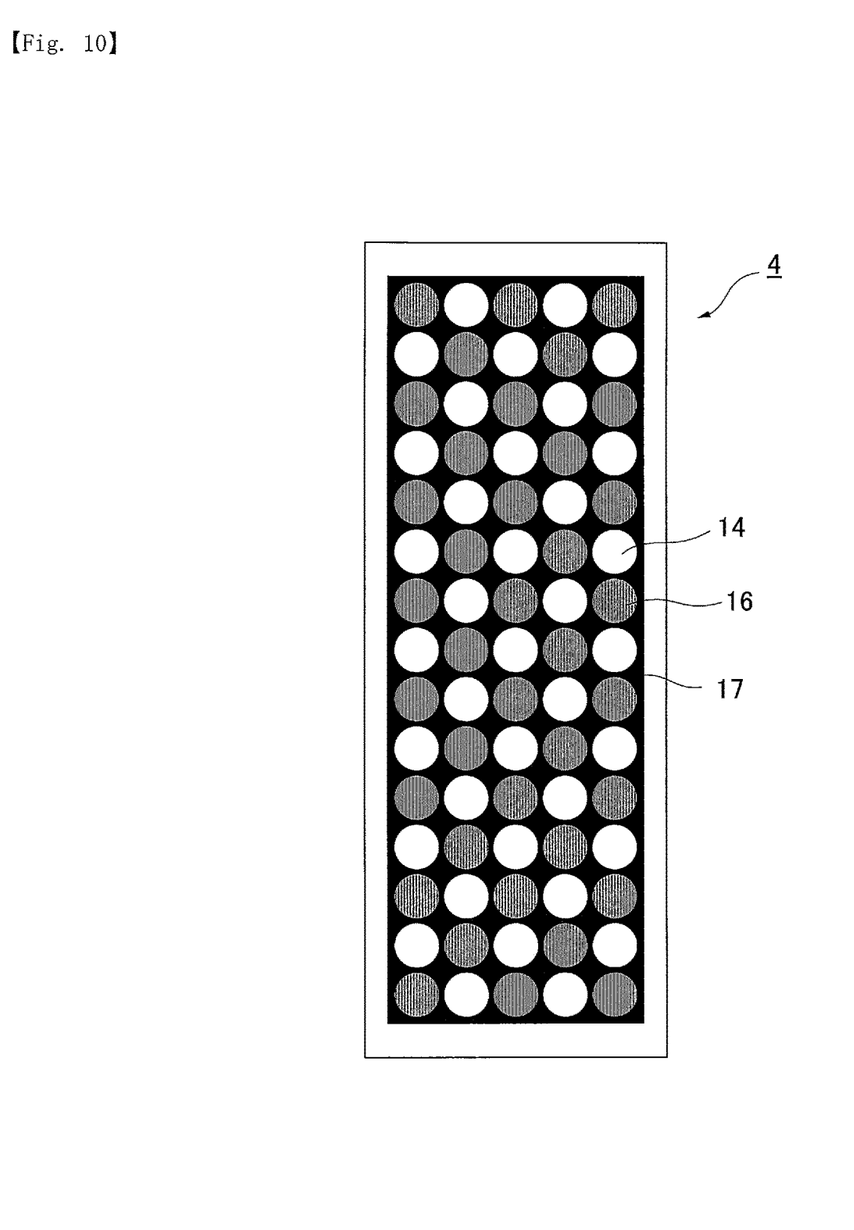
FIG. 10 is a plan view of an absorbing body 4 according to another embodiment.

(2) In the above-described embodiment, in the case where the first protrusions 14 and the second protrusions 16 are disposed alternately in a grid shape, as shown in FIG. 3, the planar shape of each of the first protrusions 14 and the second protrusions 16 is a square shape, but as shown in FIG. 10, the planar shape of each of the first protrusions 14 and the second protrusions 16 may be a circular shape or an elliptic shape.

REFERENCE SIGNS LIST

1 . . . sanitary napkin, 2 . . . liquid impermeable rear surface sheet, 3 . . . liquid permeable front surface sheet, 4 . . . absorbing body, 7 . . . side nonwoven fabric, 10 . . . upper layer sheet, 11 . . . lower layer sheet, 12 . . . highly water-absorbent polymer, 13 . . . first space part, 14 . . . first protrusion, 15 . . . second space part, 16 . . . second protrusion, 17 . . . joining part

The invention claimed is:

1. An absorbent article comprising an absorbing body with a highly water-absorbent polymer interposed between an upper layer sheet disposed on the skin side and a lower layer sheet disposed on the non-skin side,
wherein the upper layer sheet has a plurality of first protrusions forming first space parts that are to be filled with the highly water-absorbent polymer and that expand to the skin side, and a plurality of second protrusions forming second space parts, each of which having a smaller volume than each of the first space parts, that are to be filled with the highly water-absorbent polymer and that expand to the skin side, and the weight per unit area of the highly water-absorbent polymer filled into the second space parts is smaller than the weight per unit area of the highly water-absorbent polymer filled into the first space parts,
wherein the first protrusions and the second protrusions are arranged alternately in a grid shape, the first protrusions are arranged at both sides of the second protrusions in the longitudinal direction and in the width direction such that the first protrusions adjoin the second protrusions, the second protrusions are arranged to adjoin one another in an oblique direction, and a part in which the first protrusions do not intervene is provided between the adjacent second protrusions, and
wherein the expansion height of the second protrusions towards the skin side is made lower than the expansion height of the first protrusions towards the skin side, and the skin side of the absorbing body is formed into a concavo-convex shape in which the first protrusions with a relatively greater height and the second protrusions with a relatively lower height are formed.

2. The absorbent article according to claim 1, wherein the weight per unit area of the highly water-absorbent polymer filled into the first space parts is 50 to 300 g/m$^2$, and the weight per unit area of the highly water-absorbent polymer filled into the second space parts is 20 to 150 g/m$^2$.

3. The absorbent article according to claim 1, wherein the volume ratio of the first space part:the second space part is 2 to 10:1.

4. The absorbent article according to claim 1, wherein each of the outer peripheries of the first protrusions and the second protrusions is a joining part with the lower layer sheet, and the joining parts of the adjacent first protrusions or the second protrusions are provided continuously.

5. The absorbent article according to claim 1, wherein a fiber assembly layer comprising a water-absorbing fiber assembly is arranged on the non-skin side or the skin side of the absorbing body.

* * * * *